(12) United States Patent
Tani et al.

(10) Patent No.: US 9,499,469 B2
(45) Date of Patent: Nov. 22, 2016

(54) PRODUCTION METHOD OF KETOMALONIC ACID COMPOUND

(71) Applicant: IHARA CHEMICAL INDUSTRY CO., LTD., Tokyo (JP)

(72) Inventors: Shinki Tani, Fuji (JP); Minekazu Koga, Shibukawa (JP); Izumi Matsumoto, Shibukawa (JP)

(73) Assignee: IHARA CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/905,645

(22) PCT Filed: Jul. 3, 2014

(86) PCT No.: PCT/JP2014/067728
§ 371 (c)(1),
(2) Date: Jan. 15, 2016

(87) PCT Pub. No.: WO2015/008629
PCT Pub. Date: Jan. 22, 2015

(65) Prior Publication Data
US 2016/0194268 A1 Jul. 7, 2016

(30) Foreign Application Priority Data
Jul. 19, 2013 (JP) ................................. 2013-150046

(51) Int. Cl.
*C07C 69/66* (2006.01)
*C07C 67/313* (2006.01)

(52) U.S. Cl.
CPC ................................. *C07C 67/313* (2013.01)

(58) Field of Classification Search
CPC ...................................................... C07C 67/33
See application file for complete search history.

(56) References Cited

U.S. PATENT DOCUMENTS

| | | | |
|---|---|---|---|
| 4,296,114 A | 10/1981 | Appleton et al. | |
| 4,584,145 A | 4/1986 | Santi et al. | |
| 6,329,389 B1 | 12/2001 | Suzuki et al. | |
| 6,348,461 B1 | 2/2002 | Takano et al. | |
| 2012/0004443 A1 | 1/2012 | Tani | |

FOREIGN PATENT DOCUMENTS

| | | | |
|---|---|---|---|
| EP | 0 167 053 A1 | 1/1986 | |
| JP | 61-12647 A | 1/1986 | |
| JP | 8-151346 A | 6/1996 | |
| WO | 2005/021547 A2 | 3/2005 | |
| WO | 2010/150548 A1 | 12/2010 | |
| WO | WO 2010150548 A1 * | 12/2010 | ............. C07C 67/31 |

OTHER PUBLICATIONS

Notification of Transmittal of Translation of the International Preliminary Report of Patentability (Form PCT/IB/338 issued in counterpart International Patent Application No. PCT/JP2014/067728 mailed Jan. 28, 2016, with Forms PCT/IB/373 and PCT/IB/326, with English translation, (3 pages).

Witten Opinion dated Sep. 16, 2014, issued in counterpart International Patent Application No. PCT/JP2014/067728, with English translation. (6 pages).
International Search Report dated Sep. 16, 2014, issued in counterpart Application No. PCT/JP2014/067728 (1 page).
Clark-Lewis et al., "Quinoxaline Derivatives. Part IV", J. Chem. Soc., Jan. 1, 1957, pp. 430-439.
Harayama et al., "Hydrolysis Products of Flavins (Isoalloxazines)", J. Chem. Soc. Perkin Transactions 1, 1987, pp. 75-83.
Astin et al., "Selenium Dioxide, a New Oxidising Agent. Part III.", J. Chem. Soc., 1933, pp. 391-394.
Dox, " Ethyl OX0MALONATE", Organic Syntheses, 4, 1925, pp. 27-28.
Tietze et al., "Diethyl Oxomalonate", Encyclopedia of Reagents for Organic Synthesis, 2001, pp. 3711-3719.
Liu et al., "Oxidation of a-Methyl or a-Methylene Groups in Carbonyl Compounds With Ammonium Chlorochromate", Chinese Chemical Letters, vol. 3, No. 8, 1992, pp. 585-588.
Kochergin et al., "Chemistry of nitro esters. XVII. Production of mesoxalic acid esters", Chemical. Abstract, 123: 256144, (1 page).
Saba, "Synthesis of Vicinal Trioxo Compounds by Dimethyl Dioxirane Oxidation of 2-Diaz0-1,3-Dioxo Derivatives", Synthetic Communications, 1994, 24, pp. 695-699.
Tietze, et al., "An.Annual Publication of Satisfactory Methods for the Preparation of Organic Chemicals", Organic Syntheses, 71, 1993, pp. 214-219.

* cited by examiner

*Primary Examiner* — Deborah D Carr
(74) *Attorney, Agent, or Firm* — Westerman, Hattori, Daniels & Adrian, LLP

(57) ABSTRACT

Provided is a method for producing an industrially useful ketomalonic acid compound such as ketomalinic acid diesters, or a hydrate thereof, by a method more favorable from an economic and environmental standpoint and from a safety standpoint. The present invention relates to a method involving reacting a malonic acid compound represented by general formula (1)

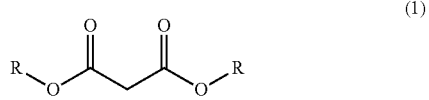

(1)

(in the formula, The each Rs indicate an alkyl group, a cycloalkyl group, etc.) with chlorine dioxide to produce a ketomalonic acid compound represented by the general formula (2)

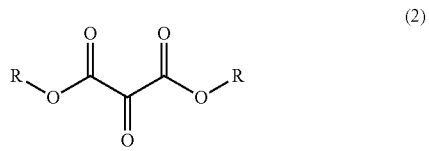

(2)

(in the formula, R has the same meaning as above), or a hydrate thereof.

13 Claims, No Drawings

PRODUCTION METHOD OF KETOMALONIC ACID COMPOUND

TECHNICAL FIELD

The present invention relates to a method of producing a ketomalonic acid compound or a hydrate thereof such as a ketomalonic acid diester through the reaction of a malonic acid compound such as a malonic acid diester with chlorine dioxide.

BACKGROUND ART

Ketomalonic acid diesters or hydrates thereof are useful compounds as raw materials in the production of pyrazine-2-one-3-carboxylic acid ester derivatives through the reaction with diamines (see Patent Documents 1 to 4 and Non Patent Documents 1 and 2). This reaction is utilized in the production of pharmaceuticals, agricultural chemicals, and the like particularly as a method of producing quinoxalinone derivatives from aromatic diamines.

Conventionally, direct or indirect methods have been reported as the method of synthesizing ketomalonic acid diesters from malonic acid diesters. However, both of them have a problem. As the method of synthesizing ketomalonic acid diesters from malonic acid diesters, for example, a method is known in which a ketomalonic acid diester is produced by oxidizing a malonic acid diester with an oxidizing agent such as selenium dioxide (for example, see Non Patent Document 3), dinitrogen trioxide (for example, see Non Patent Document 4), or chromium trioxide (for example, see Non Patent Document 6). However, all of those methods have problems such as severe toxicity of reagents, a difficulty in handling of reagents, and the like.

In addition, methods of producing a ketomalonic acid diester such as a method in which a compound obtained by substituting the active methylene moiety of a malonic acid diester with bromine is reacted with silver nitrate (for example, see Non Patent Document 7), a method in which a compound obtained by substituting the active methylene moiety of a malonic acid diester with an azo group is reacted with dimethyldioxirane (for example, see Non Patent Document 8), a method in which a compound obtained by substituting the active methylene moiety of a malonic acid diester with a methylene group is reacted with ozone (for example, see Non Patent Documents 5 and 9), and a method in which a compound obtained by substituting the active methylene moiety of a malonic acid diester with a hydroxyl group is reacted in the presence of a precious metal catalyst (for example, see Patent Document 5) are also known. However, in these methods, there is a drawback that tartronic acid that is much more expensive than malonic acid diesters is used as a raw material or the active methylene moiety of a malonic acid diester is required to be modified in advance. Hence, there are economic and operational problems in these methods. In addition, there is a problem of using an expensive reagent, a special reagent, an expensive catalyst, or a transition metal in these methods.

Furthermore, a method has been reported in which a malonic acid diester is reacted with sodium chlorite (see Patent Document 6). The method described in Patent Document 6 is superior to conventional methods known before Patent Document 6, but there is still room for improvement in consideration of economic and environmental aspects as to be described later.

CITATION LIST

Patent Document

Patent Document 1: U.S. Pat. No. 6,329,389 B1
Patent Document 2: U.S. Pat. No. 6,348,461 B1
Patent Document 3: U.S. Pat. No. 4,296,114 A
Patent Document 4: WO 2005/021547 A2
Patent Document 5: JP 8-151346 A
Patent Document 6: WO 2010/150548 A1

Non Patent Document

Non Patent Document 1: J. W. Clark-Lewis, et al., J. Chem. Soc., 1957, 430-439.
Non Patent Document 2: Fumio Yoneda, et al., J. Chem. Soc. Perkin Transactions 1, 1987, 75-83.
Non Patent Document 3: S. Astin et al., J. Chem. Soc., 1933, 391-394.
Non Patent Document 4: A. W. Dox, Organic Syntheses, 4, 1925, 27-28.
Non Patent Document 5: Encyclopedia of Reagents for Organic Synthesis, 3711 (2001).
Non Patent Document 6: Liang Xian liu et al., Chinese Chemical Letters, 3, 1992, 585-588.
Non Patent Document 7: Chem. Abstr., 123: 256144.
Non Patent Document 8: Antonio Saba, Synthetic Communications, 24, 695-699 (1994).
Non Patent Document 9: Lutz F., et al., Organic Syntheses, 71, 214-219 (1993).

SUMMARY OF THE INVENTION

Problems to be Solved by the Invention

An object of the present invention is to provide a method of producing a ketomalonic acid compound or a hydrate thereof such as a ketomalonic acid diester that is industrially useful by a more preferred method from the standpoint of economy, environment and safety.

Another object of the present invention is to provide a highly safe method of producing a ketomalonic acid compound or a hydrate thereof such as a ketomalonic acid diester, which can avoid the risk of explosion and also suppress the runaway of the reaction.

Still another object of the present invention is to provide a method of producing a ketomalonic acid compound or a hydrate thereof such as a ketomalonic acid diester, which can solve one or more drawbacks or problems in the conventional methods described above.

Means to Solving the Problems

In view of the situation described above, the present inventors have carried out extensive researches on the method of producing a ketomalonic acid compound or a hydrate thereof such as a ketomalonic acid diester. As a result, the present inventors have surprisingly found out that a ketomalonic acid compound represented by the following general formula (2) or a hydrate thereof can be produced by reacting a malonic acid compound represented by the following general formula (1) with chlorine dioxide, and have accomplished the present invention based on this finding.

Specifically, it has been found out that it is possible to safely and efficiently produce a ketomalonic acid compound or a hydrate thereof such as a ketomalonic acid diester by introducing chlorine dioxide gas while controlling the pH of an aqueous solution, a suspension, or the like which contains a malonic acid compound such as a malonic acid diester.

In other words, the present invention relates to a method of producing a ketomalonic acid compound represented by the following general formula (2)

[Chemical Formula 2]

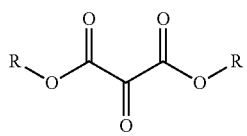

(2)

(wherein Rs may be the same or different from each other, and each represents a hydrogen atom, an alkyl group which optionally has substituent(s), a cycloalkyl group which optionally has substituent(s), an aromatic hydrocarbon group which optionally has substituent(s), or an aromatic heterocyclic group which optionally has substituent(s), and the two Rs may bind to each other to form a ring) or a hydrate thereof by reacting a malonic acid compound represented by the following general formula (1)

[Chemical Formula 1]

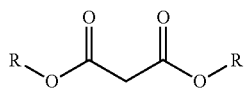

(1)

(wherein R is the same as described above) with chlorine dioxide. In particular, the present invention relates to the method of producing a ketomalonic acid compound represented by the general formula (2) or a hydrate thereof, wherein the reaction of the malonic acid compound with chlorine dioxide is conducted at pH in the range of 4 to 11 and preferably 5 to 10.

Effects of the Invention

A novel industrial production method for production of a ketomalonic acid compound or a hydrate thereof such as a ketomalonic acid diester is provided by the method of the present invention.

The present invention is characterized in that a malonic acid compound (raw material compound) represented by the general formula (1) is reacted with chlorine dioxide as an oxidizing agent. The present inventors have found out that chlorine dioxide has ability to specifically oxidize the methylene moiety of a malonic acid compound such as a malonic acid diester for the first time.

Meanwhile, a chlorite such as sodium chlorite is used as an oxidizing agent in the production method described in Patent Document 6. As the method of producing a chlorite such as sodium chlorite to be used as an oxidizing agent, for example, a method is known in which a chlorite such as sodium chlorite is produced by reacting chlorine dioxide with a base such as sodium hydroxide and a reducing agent such as hydrogen peroxide. In short, in this method, a chlorite such as sodium chlorite to be used as an oxidizing agent is produced using chlorine dioxide as a raw material and this is used as an oxidizing agent. It means that, in this method, it is required to produce a chlorite such as sodium chlorite. On the other hand, in the method of the present invention, it is possible to directly use chlorine dioxide, and thus it is not required to produce a chlorite such as sodium chlorite any longer and the desired product is more conveniently obtained.

The method of the present invention is characterized in that chlorine dioxide gas is used as an oxidizing agent in the oxidation reaction of a malonic acid compound such as a malonic acid diester. A more preferred embodiment of the method of the present invention is a method in which the pH of the reaction is controlled at pH in the range of 4 to 11 and preferably 5 to 10. It has been found out for the first time that the desired reaction efficiently proceeds by the use of chlorine dioxide in the case the reaction is conducted under pH control as presented in Examples to be described later.

In the production method described in Patent Document 6, it is indicated that it is preferable that the pH of the reaction is in an acidic region. On the other hand, in the method of the present invention, it has been discussed that the desired reaction proceeds not only in a weakly acidic region (for example, pH 5 to 6) but also from a neutral region (for example, pH 6 to 8) to a basic region (for example, pH 8 to 10). Hence, in the production method of a ketomalonic acid compound such as a ketomalonic acid diester, new alternatives are provided in relation to the pH of the reaction by the method of the present invention. For example, a neutral condition is generally preferred to an acidic condition in the chemical industry in many cases, and the method of the present invention is considered to be an industrially more preferred method. Furthermore, the stability of the ester residues of the malonic acid compound (raw material compound) represented by the general formula (1) described above, could be to be different depending on the pH. If it is true, the method of the present invention can possibly offer an alternative of a novel or preferred reaction condition. Here, the ester residues of the malonic acid compound represented by the general formula (1) described above, are R in the general formula (1) described above.

Furthermore, in the present invention, the present inventors have found out a method to safely and efficiently handle chlorine dioxide gas in the oxidation reaction of a malonic acid compound such as a malonic acid diester.

Chlorine dioxide used in the method of the present invention is a substance to be safely used as a bleaching agent of pulp, fiber, or food or a disinfectant for disinfection of water and the like when it is at a low concentration. Besides, chlorine dioxide is inexpensive and thus industrially preferred. On the other hand, chlorine dioxide is also a substance having a risk of explosion and the like when it is at a high concentration. However, according to the method of the present invention, it is possible to conduct the reaction by blowing chlorine dioxide gas at a low concentration in a required amount, thus an excess amount of chlorine dioxide is not filled in the system, the risk of explosion can be avoided, and also the runaway of the reaction can also be suppressed. Meanwhile, in an organic synthesis reaction, there is a case in which a proper measure or attention such as cooling and divided introduction or dropwise addition is required for heat generation, induction period, and the like, but such a measure or attention is facilitated according to the method of the present invention.

Hence, according to the method of the present invention, it is possible to significantly safely produce a ketomalonic acid compound or a hydrate thereof such as a ketomalonic acid diester from a malonic ac id compound such as a malonic acid diester as the risk of explosion and the runaway of reaction can be suppressed. As a result, according to the method of the present invention, it is possible to industrially produce a ketomalonic acid compound or a hydrate thereof such as a ketomalonic acid diester at a high yield, a high purity, and a favorable efficiency.

Furthermore, in the production method described in Patent Document 6, a carboxylic acid compound such as acetic acid is used. Since it is highly possible that the carboxylic acid compound used such as acetic acid becomes a waste, and the reuse thereof is not convenient, the carboxylic acid compound could be a cause of environmental contamination. However, according to the method of the present invention, it is possible to produce a desired ketomalonic acid compound such as a ketomalonic acid diester even without using a carboxylic acid compound such as acetic acid. Not to use a carboxylic acid compound such as acetic acid contributes to a decrease in cost and environmental burden.

By the method of the present invention, it is possible to solve the problems such as severe toxicity of a reagent or a difficulty in handling of a reagent predicted in industrialization and it is possible to produce a ketomalonic acid compound such as a ketomalonic acid diester without requiring a special reactant, an expensive reagent, and a transition metal such as a noble metal. In addition, by the method of the present invention, harmful waste derived from the catalyst or transition metal is also not generated, thus the waste treatment is easy, and the method is environmentally friendly and of high industrial utility value.

According to the method of the present invention, it is possible to use a readily available malonic acid compound such as a malonic acid diester represented by the general formula (1) as a raw material. A malonic acid compound such as a malonic acid diester of a raw material in the method of the present invention is a compound that is widely used in organic synthesis and is safe and readily available. In addition, in the method of the present invention, it is not required to modify the active methylene moiety of a malonic acid diester in advance and it is possible to directly use a malonic acid diester and the like in the reaction, thus the method is not economically or operationally problematic. Furthermore, in the method of the present invention, it is possible to use water as a solvent. Water is highly safe, inexpensive, and easy to handle.

Furthermore, the method of the present invention does not require high temperature or high pressure thus can select a mild reaction condition, and a ketomalonic acid compound such as a ketomalonic acid diester can be produced under a convenient condition suitable for industrialization.

As described above, the method of the present invention is significantly useful as an industrial production method.

MODES FOR CARRYING OUT THE INVENTION

Hereinafter, the present invention will be described in detail.

The present invention can be described more specifically as described below in [1] to [61].

[1] A method of producing a ketomalonic acid compound represented by the general formula (2)

[Chemical Formula 4]

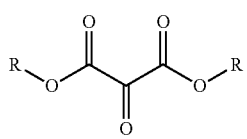

(wherein Rs may be the same or different from each other, and each represents a hydrogen atom, an alkyl group which optionally has substituent(s), a cycloalkyl group which optionally has substituent(s), an aromatic hydrocarbon group which optionally has substituent(s), or an aromatic heterocyclic group which optionally has substituent(s), and the two Rs may bind to each other to form a ring) or a hydrate thereof by reacting a malonic acid compound represented by the general formula (1)

[Chemical Formula 3]

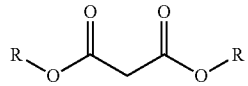

(wherein R is the same as described above) with chlorine dioxide.

[2] The method of producing a ketomalonic acid compound or a hydrate thereof according to [1], wherein the reaction of the malonic acid compound with chlorine dioxide is conducted at pH in the range of 4 to 11.

[3] The method of producing a ketomalonic acid compound or a hydrate thereof according to [1] or [2], wherein the reaction of the malonic acid compound with chlorine dioxide is conducted at pH in the range of 5 to 10.

[4] The method of producing a ketomalonic acid compound or a hydrate thereof according to any one of [1] to [3], wherein the reaction of the malonic acid compound with chlorine dioxide is conducted at pH in the range of 5 to 8.

[5] The method of producing a ketomalonic acid compound or a hydrate thereof according to any one of [1] to [4], wherein the reaction of the malonic acid compound with chlorine dioxide is conducted at pH in the range of 6 to 8.

[6] The method of producing a ketomalonic acid compound or a hydrate thereof according to any one of [1] to [5], wherein the pH is controlled using a pH adjusting agent.

[7] The method of producing a ketomalonic acid compound or a hydrate thereof according to [6], wherein an inorganic base is used as the pH adjusting agent.

[8] The method of producing a ketomalonic acid compound or a hydrate thereof according to [6] or [7], wherein an alkali metal hydroxide is used as the pH adjusting agent.

[9] The method of producing a ketomalonic acid compound or a hydrate thereof according to any one of [6] to [8], wherein sodium hydroxide or potassium hydroxide is used as the pH adjusting agent.

[10] The method of producing a ketomalonic acid compound or a hydrate thereof according to any one of [6] to [9], wherein sodium hydroxide is used as the pH adjusting agent.

[11] The method of producing a ketomalonic acid compound or a hydrate thereof according to [1], wherein the reaction of the malonic acid compound with chlorine dioxide is conducted at pH in the range of 4 to 11, wherein the pH is controlled using an inorganic base as a pH adjusting agent.

[12] The method of producing a ketomalonic acid compound or a hydrate thereof according to [1] or [11], wherein the reaction of the malonic acid compound with chlorine dioxide is conducted at pH in the range of 5 to 10, wherein the pH is controlled using an inorganic base as a pH adjusting agent.

[13] The method of producing a ketomalonic acid compound or a hydrate thereof according to any one of [1], [11], or [12], wherein the reaction of the malonic acid compound with chlorine dioxide is conducted at pH in the range of 5 to 8, wherein the pH is controlled using an inorganic base as a pH adjusting agent.

[14] The method of producing a ketomalonic acid compound or a hydrate thereof according to any one of [1], [11], [12], or [13], wherein the reaction of the malonic acid compound with chlorine dioxide is conducted at pH in the range of 6 to 8, wherein the pH is controlled using an inorganic base as a pH adjusting agent.

[15] The method of producing a ketomalonic acid compound or a hydrate thereof according to [1], wherein the reaction of the malonic acid compound with chlorine dioxide is conducted at pH in the range of 4 to 11, wherein the pH is controlled using an alkali metal hydroxide as a pH adjusting agent.

[16] The method of producing a ketomalonic acid compound or a hydrate thereof according to [1] or [15], wherein the reaction of the malonic acid compound with chlorine dioxide is conducted at pH in the range of 5 to 10, wherein the pH is controlled using an alkali metal hydroxide as a pH adjusting agent.

[17] The method of producing a ketomalonic acid compound or a hydrate thereof according to any one of [1], [15], or [16], wherein the reaction of the malonic acid compound with chlorine dioxide is conducted at pH in the range of 5 to 8, wherein the pH is controlled using an alkali metal hydroxide as a pH adjusting agent.

[18] The method of producing a ketomalonic acid compound or a hydrate thereof according to any one of [1], [15], [16], or [17], wherein the reaction of the malonic acid compound with chlorine dioxide is conducted at pH in the range of 6 to 8, wherein the pH is controlled using an alkali metal hydroxide as a pH adjusting agent.

[19] The method of producing a ketomalonic acid compound or a hydrate thereof according to [1], wherein the reaction of the malonic acid compound with chlorine dioxide is conducted at pH in the range of 4 to 11, wherein the pH is controlled using sodium hydroxide or potassium hydroxide as a pH adjusting agent.

[20] The method of producing a ketomalonic acid compound or a hydrate thereof according to [1] or [19], wherein the reaction of the malonic acid compound with chlorine dioxide is conducted at pH in the range of 5 to 10, wherein the pH is controlled using sodium hydroxide or potassium hydroxide as a pH adjusting agent.

[21] The method of producing a ketomalonic acid compound or a hydrate thereof according to any one of [1], [19], or [20], wherein the reaction of the malonic acid compound with chlorine dioxide is conducted at pH in the range of 5 to 8, wherein the pH is controlled using sodium hydroxide or potassium hydroxide as a pH adjusting agent.

[22] The method of producing a ketomalonic acid compound or a hydrate thereof according to any one of [1], [19], [20], or [21], wherein the reaction of the malonic acid compound with chlorine dioxide is conducted at pH in the range of 6 to 8, wherein the pH is controlled using sodium hydroxide or potassium hydroxide as a pH adjusting agent.

[23] The method of producing a ketomalonic acid compound or a hydrate thereof according to [1], wherein the reaction of the malonic acid compound with chlorine dioxide is conducted at pH in the range of 4 to 11, wherein the pH is controlled using sodium hydroxide as a pH adjusting agent.

[24] The method of producing a ketomalonic acid compound or a hydrate thereof according to [1] or [23], wherein the reaction of the malonic acid compound with chlorine dioxide is conducted at pH in the range of 5 to 10, wherein the pH is controlled using sodium hydroxide as a pH adjusting agent.

[25] The method of producing a ketomalonic acid compound or a hydrate thereof according to any one of [1], [23], or [24], wherein the reaction of the malonic acid compound with chlorine dioxide is conducted at pH in the range of 5 to 8, wherein the pH is controlled using sodium hydroxide as a pH adjusting agent.

[26] The method of producing a ketomalonic acid compound or a hydrate thereof according to any one of [1], [23], [24], or [25], wherein the reaction of the malonic acid compound with chlorine dioxide is conducted at pH in the range of 6 to 8, wherein the pH is controlled using sodium hydroxide as a pH adjusting agent.

[27] The method of producing a ketomalonic acid compound or a hydrate thereof according to any one of [1] to [26], wherein Rs in the general formula (1) may be the same or different from each other, wherein each of R represents any group selected from the following:

(a) a $C_1$ to $C_6$ alkyl group which optionally has substituent(s);

(b) a $C_3$ to $C_6$ cycloalkyl group which optionally has substituent(s);

(c) an aromatic hydrocarbon group having from 6 to 12 carbon atoms which optionally has substituent(s);

(d) a 5- to 10-membered aromatic heterocyclic group having from 1 to 4 heteroatoms selected from a nitrogen atom, an oxygen atom, or a sulfur atom which optionally has substituent(s); or (e) a ring wherein two Rs bind to each other to form the ring together with an adjacent oxygen atom.

[28] The method of producing a ketomalonic acid compound or a hydrate thereof according to [27], wherein the $C_1$ to $C_6$ alkyl group which optionally has substituent(s) is a $C_1$ to $C_4$ alkyl group which optionally has substituent(s).

[29] The method of producing a ketomalonic acid compound or a hydrate thereof according to [27] or [28], wherein the substituent in R in the general formula (1) is a group selected from the group consisting of a halogen atom, a $C_1$ to $C_6$ alkyl group, a $C_3$ to $C_6$ cycloalkyl group, a $C_1$ to $C_6$ haloalkyl group, a hydroxyl group, a $C_1$ to $C_6$ alkoxy group, and an aromatic hydrocarbon group having from 6 to 12 carbon atoms.

[30] The method of producing a ketomalonic acid compound or a hydrate thereof according to any one of [1] to [29], wherein R in the general formula (1) is a $C_1$ to $C_4$ alkyl group.

[31] The method of producing a ketomalonic acid compound or a hydrate thereof according to any one of [1] to [30], wherein R in the general formula (1) is a methyl or an ethyl.

[32] The method of producing a ketomalonic acid compound or a hydrate thereof according to any one of [1] to [31], wherein the reaction of the malonic acid compound with chlorine dioxide is conducted at a temperature of from 0° C. to 40° C.

[33] The method of producing a ketomalonic acid compound or a hydrate thereof according to any one of [1] to [32], wherein the reaction of the malonic acid compound with chlorine dioxide is conducted at a temperature of from 5° C. to 35° C.

[34] The method of producing a ketomalonic acid compound or a hydrate thereof according to any one of [1] to [33], wherein the reaction of the malonic acid compound with chlorine dioxide is conducted at a temperature of from 10° C. to 25° C.

[35] The method of producing a ketomalonic acid compound or a hydrate thereof according to any one of [1] to [34], wherein the reaction of the malonic acid compound with chlorine dioxide is conducted for 0.5 hours to 100 hours.

[36] The method of producing a ketomalonic acid compound or a hydrate thereof according to any one of [1] to [35], wherein the reaction of the malonic acid compound with chlorine dioxide is conducted for 4 hours to 48 hours.

[37] The method of producing a ketomalonic acid compound or a hydrate thereof according to any one of [1] to [36], wherein the reaction of the malonic acid compound with chlorine dioxide is conducted for 4 hours to 12 hours.

[38] The method of producing a ketomalonic acid compound or a hydrate thereof according to any one of [1] to [37], wherein chlorine dioxide is blown into a reaction mixture in a gaseous form as chlorine dioxide gas.

[39] The method of producing a ketomalonic acid compound or a hydrate thereof according to [38], wherein a concentration of chlorine dioxide gas is 10 (vol %) or less.

[40] The method of producing a ketomalonic acid compound or a hydrate thereof according to [38] or [39], wherein a concentration of chlorine dioxide gas is in the range of 2 (vol %) to 10 (vol %).

[41] The method of producing a ketomalonic acid compound or a hydrate thereof according to any one of [38] to [40], wherein a concentration of chlorine dioxide gas is in the range of 5 (vol %) to 10 (vol %).

[42] The method of producing a ketomalonic acid compound or a hydrate thereof according to any one of [38] to [41], wherein gas to be used in the dilution of chlorine dioxide gas is one kind or two or more kinds of inert gases selected from the group consisting of air, nitrogen, argon, helium, and carbon dioxide.

[43] The method of producing a ketomalonic acid compound or a hydrate thereof according to any one of [38] to [42], wherein gas to be used in the dilution of chlorine dioxide gas is air and/or nitrogen.

[44] The method of producing a ketomalonic acid compound or a hydrate thereof according to any one of [38] to [43], wherein gas to be used in the dilution of chlorine dioxide gas is nitrogen.

[45] The method of producing a ketomalonic acid compound or a hydrate thereof according to any one of [38] to [44], wherein a purity of chlorine dioxide gas is 70% or more.

[46] The method of producing a ketomalonic acid compound or a hydrate thereof according to any one of [38] to [45], wherein a purity of chlorine dioxide gas is 90% or more.

[47] The method of producing a ketomalonic acid compound or a hydrate thereof according to any one of [38] to [46], wherein chlorine dioxide gas does not substantially contain chlorine gas.

[48] The method of producing a ketomalonic acid compound or a hydrate thereof according to any one of [1] to [47], wherein chlorine dioxide is chlorine dioxide gas in which a concentration of chlorine dioxide gas is in the range of 2 (vol %) to 10 (vol %) and a purity of chlorine dioxide gas is in the range of 70% to 100%.

[49] The method of producing a ketomalonic acid compound or a hydrate thereof according to any one of [1] to [48], wherein chlorine dioxide is chlorine dioxide gas in which a concentration of chlorine dioxide gas is in a range of 2 (vol %) to 10 (vol %) and a purity of chlorine dioxide gas is in the range of 90% to 100%.

[50] The method of producing a ketomalonic acid compound or a hydrate thereof according to any one of [1] to [49], wherein chlorine dioxide is chlorine dioxide gas in which a concentration of chlorine dioxide gas is in the range of 5 (vol %) to 10 (vol %) and a purity of chlorine dioxide gas is in the range of 70% to 100%.

[51] The method of producing a ketomalonic acid compound or a hydrate thereof according to any one of [1] to [50], wherein chlorine dioxide is chlorine dioxide gas in which a concentration of chlorine dioxide gas is in the range of 5 (vol %) to 10 (vol %) and a purity of chlorine dioxide gas is in the range of 90% to 100%.

[52] The method of producing a ketomalonic acid compound or a hydrate thereof according to any one of [38] to [51], wherein chlorine dioxide gas is one obtained by diluting chlorine dioxide gas generated through the following any method:

(a) a method of generating chlorine dioxide gas from an aqueous solution of a salt of chlorous acid and an inorganic strong acid;

(b) a method of generating chlorine dioxide gas from an aqueous solution of a salt of chloric acid, an inorganic strong acid, and hydrogen peroxide; or (c) a method of generating chlorine dioxide gas from an aqueous solution of a salt of chloric acid and an inorganic strong acid.

[53] The method of producing a ketomalonic acid compound or a hydrate thereof according to any one of [38] to [52], wherein chlorine dioxide gas is one obtained by diluting chlorine dioxide gas generated through a method to generate chlorine dioxide gas by dropwise addition of an inorganic strong acid and hydrogen peroxide to an aqueous solution of a salt of chloric acid.

[54] The method of producing a ketomalonic acid compound or a hydrate thereof according to [52] or [53], wherein the salt is an alkali metal salt.

[55] The method of producing a ketomalonic acid compound or a hydrate thereof according to [54], wherein the alkali metal salt is a sodium salt.

[56] The method of producing a ketomalonic acid compound or a hydrate thereof according to any one of [52] to [55], wherein the inorganic strong acid is hydrochloric acid or sulfuric acid.

[57] The method of producing a ketomalonic acid compound or a hydrate thereof according to [56], wherein the inorganic strong acid is hydrochloric acid.

[58] The method of producing a ketomalonic acid compound or a hydrate thereof according to any one of [1] to [57], wherein the solvent is water.

[59] The method of producing a ketomalonic acid compound or a hydrate thereof according to any one of [1] to [58], wherein the reaction of the malonic acid compound with chlorine dioxide is conducted in the presence of water.

[60] The method of producing a ketomalonic acid compound or a hydrate thereof according to any one of [32] to [59], wherein R in the general formula (1) is a $C_1$ to $C_4$ alkyl group.

[61] The method of producing a ketomalonic acid compound or a hydrate thereof according to any one of [32] to [60], wherein R in the general formula (1) is methyl or ethyl.

The terms and symbols used in the present specification will be described below.

The term "$C_a$ to $C_b$" shows that the number of carbon atoms is from a to b. For example, the term "$C_1$ to $C_4$" shows that the number of carbon atoms is from 1 to 4.

Examples of the alkyl group may include a $C_1$ to $C_6$ alkyl group and preferably a $C_1$ to $C_4$ alkyl group. The $C_1$ to $C_6$ alkyl group means a straight chain or branched chain alkyl group having from 1 to 6 carbon atoms. The $C_1$ to $C_4$ alkyl group means a straight chain or branched chain alkyl group having from 1 to 4 carbon atoms. Specific examples of the alkyl group may include methyl, ethyl, propyl, isopropyl, butyl, sec-butyl, isobutyl, tert-butyl, pentyl, hexyl and the like, preferably, methyl, ethyl, propyl, isopropyl, butyl, sec-butyl, isobutyl, and tert-butyl, more preferably, methyl, ethyl, propyl, isopropyl, and even more preferably, methyl and ethyl.

Examples of the cycloalkyl group may include a $C_3$ to $C_6$ cycloalkyl group. The $C_3$ to $C_6$ cycloalkyl group means a cycloalkyl group having from 3 to 6 carbon atoms. Specific examples of the $C_3$ to $C_6$ cycloalkyl group may include cyclopropyl, cyclobutyl, cyclopentyl, and cyclohexyl.

Examples of the aromatic hydrocarbon group may include an aromatic hydrocarbon group having from 6 to 12 carbon atoms. Specific examples of the aromatic hydrocarbon group may include phenyl, 1-naphthyl, 2-naphthyl, biphenyl and the like. The aromatic hydrocarbon group is preferably a phenyl.

Examples of the aromatic heterocyclic group may include a 5- to 10-membered aromatic heterocyclic group having one or more (for example, 1 to 4) heteroatoms selected from a nitrogen atom, an oxygen atom, or a sulfur atom in addition to carbon atoms. Specific examples of the aromatic heterocyclic group may include a furyl group, a thienyl group, a pyrazolyl group, a pyridyl group, a quinolinyl group and the like. More specific examples of the aromatic heterocyclic group may include 2- or 3-furyl, 2- or 3-thienyl, 1-, 3-, 4-, or 5-pyrazolyl, 2-, 3-, or 4-pyridyl, 2- or 8-quinolyl and the like. Preferred examples of the aromatic heterocyclic group may include 2- or 4-pyridyl, and the aromatic heterocyclic group is more preferably 2-pyridyl.

The halogen atom represents a fluorine atom, a chlorine atom, a bromine atom, or an iodine atom.

Examples of the haloalkyl group may include a $C_1$ to $C_4$ haloalkyl group. The $C_1$ to $C_4$ haloalkyl group means a straight chain or branched chain alkyl group having from 1 to 4 carbon atoms which is substituted with from 1 to 9 halogen atoms that are the same as or different from one another (wherein, the halogen atom has the same meaning as that described above.). Examples of the $C_1$ to $C_4$ haloalkyl group may include fluoromethyl, chloromethyl, bromomethyl, difluoromethyl, trifluoromethyl, chlorodifluoromethyl, 1-fluoroethyl, 2-fluoroethyl, 1-chloroethyl, 2-chloroethyl, 2,2,2-trifluoroethyl, pentafluoroethyl, 3-fluoropropyl, 3-chloropropyl, 2,2,3,3,3-pentafluoropropyl, a heptafluoropropyl, 2,2,2-trifluoro-1-trifluoromethylethyl, 4-fluorobutyl, 4-chlorobutyl, 2,2,3,3,4,4,4-heptafluorobutyl, nonafluorobutyl, 2,2,2-trifluoro-1,1-di(trifluoromethyl)ethyl and the like.

Examples of the alkoxy group may include a $C_1$ to $C_4$ alkoxy group and the like. The $C_1$ to $C_4$ alkoxy group means a ($C_1$ to $C_4$ alkyl)-O— group (wherein, the $C_1$ to $C_4$ alkyl has the same meaning as that described above.). The $C_1$ to $C_4$ alkoxy group is methoxy, ethoxy, propoxy, isopropoxy, butoxy, sec-butoxy, isobutoxy, or tert-butoxy.

Examples of the substituent in the expression "which optionally has substituent(s)" may include a halogen atom, an alkyl group, a cycloalkyl group, a haloalkyl group, an alkoxy group, an aromatic hydrocarbon group, and an aromatic heterocyclic group and the like. Wherein, all of them have the same meaning as those described above. Furthermore, examples of the substituent in the expression "which optionally has substituent(s)" may include a hydroxyl group and the like.

The expression "two Rs may bind to each other to form a ring" refers to that two R groups are linked to each other to form a divalent group, and this forms a ring together with an adjacent oxygen atom. Examples of the divalent group formed through the linkage of two R groups may include an alkylene group having from 1 to 6 carbon atoms which optionally has substituent(s), such as a methylene group or an ethylene group. The alkylene group optionally has the substituent(s) as described above, for example, a halogen atom, an alkyl group, a cycloalkyl group, a haloalkyl group, an alkoxy group, and an aromatic hydrocarbon group and the like.

(Malonic Acid Compound)

Next, the malonic acid compound represented by the above-mentioned general formula (1) (hereinafter, referred to as the "raw material compound" in some cases.) that is used as a raw material of the method of the present invention will be described.

Rs in the general formula (1) may be the same or different from each other and each represents a hydrogen atom, an alkyl group which optionally has substituent(s), a cycloalkyl group which optionally has substituent(s), an aromatic hydrocarbon group which optionally has substituent(s), or an aromatic heterocyclic group which optionally has substituent(s), and the two Rs may bind to each other to form a ring.

Preferred examples of R in the general formula (1) may include a $C_1$ to $C_4$ alkyl group, more preferably methyl, ethyl, propyl, and isopropyl, and even more preferably methyl and ethyl.

Specific examples of the malonic acid compound represented by the general formula (1) may include malonic acid, dimethyl malonate, diethyl malonate, dipropyl malonate, diisopropyl malonate, dibutyl malonate, diisobutyl malonate, di-sec-butyl malonate, di-tert-butyl malonate, dipentyl malonate, dihexyl malonate, dicyclopropyl malonate, dicyclopentyl malonate, dicyclohexyl malonate, diphenyl malonate, di(4-pyridyl) malonate, di(2-pyridyl) malonate, methyl ethyl malonate, methyl propyl malonate, methyl tert-butyl malonate, ethyl propyl malonate, ethyl tert-butyl malonate, methyl phenyl malonate, methyl (4-pyridyl) malonate, methyl (2-pyridyl) malonate, Meldrum's acid (2,2-dimethyl-1,3-dioxane-4,6-dione) and the like, but it is not limited to these.

Preferred examples of the malonic acid compound may include a dialkyl malonate (for example, dimethyl malonate, diethyl malonate, dipropyl malonate, diisopropyl malonate, dibutyl malonate, diisobutyl malonate, di-sec-butyl malonate, di-tert-butyl malonate, dipentyl malonate, dihexyl malonate, methyl ethyl malonate, methyl propyl malonate, methyl-tert-butyl malonate, ethyl propyl malonate, or ethyl-tert-butyl malonate), more preferably dimethyl malonate, diethyl malonate, dipropyl malonate, diisopropyl malonate, dibutyl malonate, diisobutyl malonate, di-sec-butyl malonate, di-tert-butyl malonate, methyl tert-butyl malonate, and ethyl tert-butyl malonate, even more preferably dimethyl malonate, diethyl malonate, dipropyl malonate, diisopropyl malonate, dibutyl malonate, di-tert-butyl malonate, methyl-tert-butylmalonate, and ethyl-tert-butyl malonate, even more preferably dimethyl malonate, diethyl malonate, dipropyl malonate, and diisopropyl malonate, and particularly preferably dimethyl malonate and diethyl malonate.

The malonic acid compound represented by the general formula (1) (raw material compound) may be a known compound or can be produced by a conventional method from a known compound (for example, esterification of malonic acid by an ordinary method and the like).

Incidentally, the malonic acid compound represented by the general formula (1) (raw material compound) may be used singly or as a mixture having any mixing ratio.

(Ketomalonic Acid Compound)

Next, the ketomalonic acid compound represented by the general formula (2) that is the desired product produced by the method of the present invention will be described.

Rs in the general formula (2) may be the same or different from each other and each represents a hydrogen atom, an alkyl group which optionally has substituent(s), a cycloalkyl group which optionally has substituent(s), an aromatic hydrocarbon group which optionally has substituent(s), or an aromatic heterocyclic group which optionally has substituent(s), and the two Rs may bind to each other to form a ring.

Preferred examples of R in the general formula (2) may include a $C_1$ to $C_4$ alkyl group, more preferably methyl, ethyl, propyl, and isopropyl, and even more preferably methyl and ethyl.

Specific examples of the ketomalonic acid compound represented by the general formula (2) may include ketomalonic acid, dimethyl ketomalonate, diethyl ketomalonate, dipropyl ketomalonate, di isopropyl ketomalonate, dibutyl ketomalonate, diisobutyl ketomalonate, di-sec-butyl ketomalonate, di-tert-butyl ketomalonate, dipentyl ketomalonate, dihexyl ketomalonate, dicyclopropyl ketomalonate, dicyclopentyl ketomalonate, dicyclohexyl ketomalonate, diphenyl ketomalonate, di(4-pyridyl) ketomalonate, di(2-pyridyl) ketomalonate, methyl ethyl ketomalonate, methyl propyl ketomalonate, methyl tert-butyl ketomalonate, ethyl propyl ketomalonate, ethyl tert-butyl ketomalonate, methyl phenyl ketomalonate, methyl (4-pyridyl) ketomalonate, methyl (2-pyridyl) ketomalonate and the like, but it is not limited to these.

Preferred examples of the ketomalonic acid compound may include a dialkyl ketomalonate (for example, dimethyl ketomalonate, diethyl ketomalonate, dipropyl ketomalonate, diisopropyl ketomalonate, dibutyl ketomalonate, diisobutyl ketomalonate, di-sec-butyl ketomalonate, di-tert-butyl ketomalonate, dipentyl ketomalonate, dihexyl ketomalonate, methyl ethyl ketomalonate, methyl propyl ketomalonate, methyl tert-butyl ketomalonate, ethyl propyl ketomalonate, ethyl tert-butyl ketomalonate and the like), more preferably dimethyl ketomalonate, diethyl ketomalonate, dipropyl ketomalonate, diisopropyl ketomalonate, dibutyl ketomalonate, diisobutyl ketomalonate, di-sec-butyl ketomalonate, di-tert-butyl ketomalonate, methyl-tert-butyl ketomalonate, and ethyl-tert-butyl ketomalonate, even more preferably dimethyl ketomalonate, diethyl ketomalonate, dipropyl ketomalonate, diisopropyl ketomalonate, dibutyl ketomalonate, di-tert-butyl ketomalonate, methyl-tert-butyl ketomalonate, and ethyl-tert-butyl ketomalonate, even more preferably dimethyl ketomalonate, diethyl ketomalonate, dipropyl ketomalonate, and di isopropyl ketomalonate, and particularly preferably dimethyl ketomalonate and diethyl ketomalonate.

Incidentally, the ketomalonic acid compound that is represented by the general formula (2) and produced by the method of the present invention may be a single substance or a mixture having any proportion.

(Hydrate)

Next, the hydrate of a ketomalonic acid compound represented by the general formula (2) that is the desired product produced by the method of the present invention will be described.

The ketomalonic acid compound that is produced by the method of the present invention and represented by the general formula (2) is a compound having a keto group between two ester groups and the like, in the other words, a compound having electron-withdrawing groups at a position adjacent to a keto group. Hence, the ketomalonic acid compound represented by the general formula (2) forms a hydrate of a ketomalonic acid compound represented by the following general formula (3) in the presence of water.

[Chemical Formula 5]

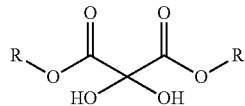

(3)

(Wherein, Rs have the same meaning as those described above). This hydrate can be converted into the ketomalonic acid compound represented by the general formula (2) of a keto type, for example, by being subjected to the dehydration treatment such as a heat treatment if necessary. Such a reversible reaction is the same as the general nature of a hydrate such as chloral hydrate.

In general, the product is obtained in the form of a hydrate of a ketomalonic acid compound represented by the general formula (3) when the reaction of the present invention is conducted in the presence of water. On the other hand, in general, the product is obtained in the form of the ketomalonic acid compound represented by the general formula (2) when the reaction of the present invention is conducted under an anhydrous condition.

Furthermore, in a case in which it is desired that the reaction of the present invention is conducted in the presence of water and the product is isolated in the form of the ketomalonic acid compound represented by the general formula (2), it is possible to easily obtain the product in the form of the ketomalonic acid compound represented by the general formula (2) specifically by conducting, for example, the dehydration treatment such as azeotropic dehydration with toluene in the post-treatment after the reaction.

Namely, in the method of the present invention, it is possible to obtain the isolated product in any desired form between a form of the ketomalonic acid compound represented by the general formula (2) described above, or a form of the hydrate of a ketomalonic acid compound represented by the general formula (3) described above, by properly selecting the reaction solvent or the method of the post-treatment after the reaction.

(Chlorine Dioxide)

Next, chlorine dioxide used in the method of the present invention will be described.

As the method of producing chlorine dioxide, there is a method in which chlorine dioxide is generated by dropwise addition of hydrochloric acid to an aqueous solution of sodium chlorite or a method in which chlorine dioxide is generated by dropwise addition of hydrochloric acid and hydrogen peroxide to an aqueous solution of sodium chlorate. In addition, a method is also known in which sulfuric acid is used instead of hydrochloric acid in the method to use an aqueous solution of sodium chlorate, hydrochloric acid, and hydrogen peroxide. Furthermore, a method is also known in which chlorine dioxide and chlorine are generated from an aqueous solution of sodium chlorate and hydrochloric acid without using hydrogen peroxide, and then chlorine is removed by washing with water. Any of these methods may be used as long as the desired reaction sufficiently proceeds, and it is not limited to these as well.

The form of chlorine dioxide used in the method of the present invention is preferably a form in which the desired reaction sufficiently and safely proceeds. As the form of chlorine dioxide, a gas or a liquid is known. However, from the standpoint of safety and the like, it is preferably a gas. In addition, as the form of chlorine dioxide, chlorine dioxide may be diluted with a gas or a liquid other than chlorine dioxide.

Examples of the gas used in the dilution of chlorine dioxide may include air or nitrogen or an inert gas such as argon, helium, or carbon dioxide. From the standpoint of availability, ease of handling, safety, price, or the like, preferred examples of the gas used in the dilution of chlorine dioxide may include air or nitrogen and more preferably nitrogen, but it is not limited to these. Incidentally, the gas used in the dilution of chlorine dioxide may be used singly or by being mixed at any mixing ratio.

The liquid used in the dilution of chlorine dioxide is preferably water from the standpoint of availability, ease of handling, safety, price, the stability of chlorine dioxide in the solution, or the like. In other words, the form of chlorine dioxide may be a solution, and in this case, it is preferably an aqueous solution. However, it is not intended to exclude a solvent other than water which will be described later as the liquid used in the dilution of chlorine dioxide as long as the desired reaction proceeds. Hence, a solution of a solvent other than water is also encompassed within the scope of the present invention as the form of chlorine dioxide.

The form of chlorine dioxide used in the method of the present invention is particularly preferably a diluted gas from the standpoint of availability, ease of handling, safety, price, or the like.

The method of using chlorine dioxide used in the method of the present invention is not limited, but it is particularly preferable to introduce chlorine dioxide into the reaction system as diluted chlorine dioxide gas. The method of introducing diluted chlorine dioxide gas may be either of the blowing of diluted chlorine dioxide gas into the gas phase of the reaction system or the blowing of diluted chlorine dioxide gas into the reaction liquid (for example, bubbling and the like).

The gas concentration of chlorine dioxide gas to be introduced may include preferably the range of 2 (vol %) to 10 (vol %) and more preferably 5 (vol %) to 10 (vol %). It is preferable to handle chlorine dioxide at 10 (vol %) or less since chlorine dioxide has a characteristic to be explosive at a high concentration. However, as a result of discussion on the method of the present invention, it is presumed that the progress of the reaction slows down at a concentration of less than 2 (vol %) since chlorine dioxide is too thin.

The gas purity of chlorine dioxide gas to be introduced is preferably in the range of 70% to 100%. As a result of discussion on the method of the present invention, chlorine dioxide gas which does not substantially contain chlorine gas is preferable in order to avoid a side reaction by chlorine gas or the like that are contained as impurities. It is possible to remove chlorine gas contained in chlorine dioxide gas by washing with water. It is preferred that the gas purity of chlorine dioxide gas is 70% or more, more preferably 90% or more, namely, more preferably from 90% to 100%. Here, the gas purity of chlorine dioxide gas indicates the value calculated without taking into account of the gases used in the generation and dilution of chlorine dioxide gas.

(Amount of Chlorine Dioxide Used)

The amount of chlorine dioxide used in the method of the present invention may be in a range in which the reaction sufficiently proceeds, but for example, it is usually in the range of 1 mol to 20 mol, preferably 1 mol to 10 mol, more preferably 1 mol to 7 mol, even more preferably 1 mol to 3 mol, and even furthermore preferably 1 mol to 2 mol per 1 mol of the raw material compound represented by the general formula (1).

(pH)

Next, the pH in the method of the present invention will be described.

It is preferable that the reaction of the present invention is conducted in a proper pH range. The pH at which the reaction of the present invention is conducted is, for example, in the range of 4 to 11, preferably 5 to 10, more preferably 5 to 8, even more preferably 6 to 8 from the standpoint of reactivity, suppression of by-product, safety and the like.

In addition, examples of the pH in the method of the present invention may include the range of 7 to 11, preferably 8 to 11, more preferably 9 to 11, and even more preferably 9 to 10 before chlorine dioxide is introduced and also in the range of 4 to 11, preferably 5 to 10, more preferably 5 to 8, and even more preferably 6 to 8 at the time of reaction which proceeds as chlorine dioxide gas is introduced, but it is not limited to these.

The reaction mechanism and the like in the present invention are not clear, but the pH in the method of the present invention is presumed as follows when the method of the present invention is considered. In a case in which the pH is too low (for example, in the case of an acidic region in which the pH is less than 5), it is presumed that the active methylene moiety of a malonic acid diester is hardly activated and the reaction does not favorably proceed in some cases. In addition, in a case in which the pH is high (for example, in a case in which the reaction is conducted in an alkaline region in which the pH is greater than 9), it is considered that a by-product is easily produced by a side reaction and thus the yield decreases in some cases.

(pH Adjusting Agent)

Next, the pH adjusting agent used in the method of the present invention will be described.

The pH adjusting agent to control the pH may be any pH adjusting agent as long as the desired reaction sufficiently proceeds, but an inorganic reagent exhibiting alkalinity (namely, an inorganic base) is suitable.

Examples of the inorganic base as the pH adjusting agent may include an alkali metal hydroxide, an alkaline earth metal hydroxide, an alkali metal carbonate salt, an alkaline earth metal carbonate salt and the like.

Examples of the alkali metal hydroxide may include sodium hydroxide, potassium hydroxide, lithium hydroxide and the like.

Examples of the alkaline earth metal hydroxide may include calcium hydroxide, magnesium hydroxide, barium hydroxide and the like.

Examples of the alkali metal carbonate salt may include sodium carbonate, potassium carbonate, lithium carbonate, sodium hydrogen carbonate, potassium hydrogen carbonate, lithium hydrogen carbonate and the like.

Examples of the alkaline earth metal carbonate salt may include calcium carbonate, magnesium carbonate, barium carbonate, calcium hydrogen carbonate, magnesium hydrogen carbonate, barium hydrogen carbonate and the like.

From the standpoint of availability, ease of handling, price, or the like, for example, the pH adjusting agent is preferably an alkali metal hydroxide, specifically sodium hydroxide or potassium hydroxide is more preferable, and sodium hydroxide is even more preferable.

The form of the pH adjusting agent used in the method of the present invention may be any form as long as the desired reaction sufficiently proceeds. However, from the standpoint of availability, ease of handling, price, or the like, it is preferable to use the pH adjusting agent used in the method of the present invention usually as an aqueous solution. Examples of the concentration of the pH adjusting agent when being used as an aqueous solution may include the range of 0.1% to 60%, preferably 0.1% to 50%, more preferably 0.1% to 30%, even more preferably 1% to 30%, and even further more preferably 1% to 10%. In other words, it is preferable to use the pH adjusting agent usually as an aqueous solution at several %.

Incidentally, the pH adjusting agent may be used singly or by being mixed at any mixing ratio.

(Amount of pH Adjusting Agent Used)

The amount of the pH adjusting agent used in the method of the present invention may be in a range in which the reaction sufficiently proceeds, but examples thereof may include a range of usually 1 equivalent or more, preferably from 1 equivalent to 5 equivalents, more preferably from 1 equivalent to 2 equivalents, even more preferably from 1.2 equivalents to 1.5 equivalents per 1 mol of chlorine dioxide used.

The reaction of the present invention may be conducted, for example, by adding a pH adjusting agent at the same time while blowing chlorine dioxide into an aqueous suspension of a malonic acid compound such as a malonic acid diester. Furthermore, it is also possible to obtain a ketomalonic acid compound such as a ketomalonic acid diester, for example, by adding a malonic acid compound such as a malonic acid diester and a pH adjusting agent at the same time while blowing chlorine dioxide into a water solvent or the like. However, as a result of discussion on the method of the present invention, from the standpoint of generation of by-product, it is more preferable to avoid putting the reaction system in an alkaline atmosphere for a long time by introducing the pH adjusting agent such as an alkali metal hydroxide (for example, sodium hydroxide) in advance.

(Solvent)

Next, the solvent in the method of the present invention will be described.

For example, from the standpoint of smooth progress of the reaction and the like, the method of the present invention can be implemented in the presence of a solvent. However, the implementation of the method in the absence of a solvent is not excluded.

The solvent which can be used in the method of the present invention is preferably water from the standpoint of availability, ease of handling, price, the stability of chlorine dioxide in the solution and the like. However, the use of a solvent other than water which will be described later is not excluded as long as the desired reaction proceeds. Hence, the implementation of the method in the presence of a solvent other than water is also encompassed within the scope of the invention.

Examples of the solvent other than water may include nitriles, alcohols, carboxylic acid esters, carbonic acid esters, amides, alkyl ureas, phosphoric acid amides, sulfoxides, sulfones, ethers, ketones, carboxylic acids, aromatic hydrocarbons, halogenated aromatic hydrocarbons, aliphatic hydrocarbons, halogenated aliphatic hydrocarbons and the like, but it is not limited to these.

Examples of the nitriles may include acetonitrile, propionitrile and the like, and preferably acetonitrile.

Examples of the alcohols may include methanol, ethanol, propanol, isopropanol, butanol, tert-butanol, ethylene glycol and the like, and preferably methanol.

Examples of the carboxylic acid esters may include acetic acid esters and the like, specifically methyl acetate, ethyl acetate, butyl acetate and the like, and preferably ethyl acetate.

Examples of the carbonic acid esters may include ethylene carbonate, propylene carbonate and the like.

Examples of the amides may include N,N-dimethyl formamide (DMF), N,N-diethylformamide, N,N-dimethylacetamide (DMAC), N-methylpyrrolidone (NMP) and the like, preferably N,N-dimethylformamide, N,N-dimethylacetamide, and N-methylpyrrolidone, and more preferably N,N-dimethylformamide.

Examples of the alkyl ureas may include tetramethylurea and N,N'-dimethylimidazolidinone (DMI) and the like.

Examples of the phosphoric acid amides may include hexamethylphosphoric triamide (HMPA) and the like.

Examples of the sulfoxides may include dimethyl sulfoxide and the like.

Examples of the sulfones may include sulfolane and dimethyl sulfone and the like.

Examples of the ethers may include tetrahydrofuran (THF), 2-methyltetrahydrofuran, 1,4-dioxane, diethyl ether, dipropyl ether, diisopropyl ether, dibutyl ether, di-tert-butyl ether, diphenyl ether, cyclopentyl methyl ether (CPME), methyl tert-butyl ether, 1,2-dimethoxyethane (DME), diglyme and the like and preferably tetrahydrofuran.

Examples of the ketones may include acetone, ethyl methyl ketone, isopropyl methyl ketone, isobutyl methyl ketone (MIBK), cyclohexanone and the like and preferably acetone and isobutyl methyl ketone.

Examples of the carboxylic acids may include formic acid, acetic acid, propionic acid and the like and preferably acetic acid.

Examples of the aromatic hydrocarbons may include benzene, toluene, xylene, ethylbenzene, cumene, trimethylbenzene and the like and preferably toluene and xylene.

Examples of the halogenated aromatic hydrocarbons may include chlorobenzene, dichlorobenzene, trichlorobenzene and the like. Preferred examples thereof may include chlorobenzene.

Examples of the aliphatic hydrocarbons may include pentane, hexane, octane, decane, dodecane, isododecane, hexadecane, isohexadecane, cyclohexane, ethylcyclohexane, methyl decalin, dimethyl decalin and the like.

Examples of the halogenated aliphatic hydrocarbon may include dichloromethane, chloroform, carbon tetrachloride, and 1,2-dichloroethane and preferably dichloromethane.

In the method of the present invention, the use of a solvent other than water is also acceptable as long as the desired reaction proceeds. However, a polar solvent is preferable from the standpoint of affinity, solubility, reactivity, or the like, but it is not limited thereto.

The polar solvent used in the present specification refers to a solvent which has a specific dielectric constant of 5 or more. The specific dielectric constant adopt the value described in the "Chemical Handbook" (Fundamentals) edited by the Chemical Society of Japan, revised $5^{th}$ edition, I, PP. 770 to 777 (2004), MARUZEN Co., Ltd. The specific dielectric constant of the solvent used in the method of the present invention is, for example, usually 5 or more, preferably 7 or more, more preferably 17 or more, and even more preferably 20 or more.

As described above, the most preferable solvent used in the method of the present invention is water since it is convenient, inexpensive, and safe.

In addition, when the reaction of the present invention is conducted in the presence of a water solvent, it is also possible to select the form of the isolated product between a form of the ketomalonic acid compound represented by the general formula (2) and a form of the hydrate of a ketomalonic acid compound represented by the general formula (3) described above, by selecting a proper condition for post-treatment as described above. Hence, it is preferable to implement the method of the present invention in the presence of a water solvent.

Incidentally, the solvent may be used singly or by being mixed at any mixing ratio as long as the desired reaction proceeds. For example, when water is used as the solvent, it is not also excluded to concurrently use a water-miscible organic solvent (for example, water-miscible organic solvent such as THF, methanol, DMF and the like). In addition, for example, the reaction in a two-layer system such as a system consisting of a water solvent and a water-immiscible solvent is not also excluded.

In addition, the reaction system may be any form of a suspension, an emulsion, a homogeneous solution, or another system.

(Amount of Solvent)

The amount of solvent in the method of the present invention may be an amount in which the reaction system can be sufficiently stirred, and for example, it is usually in the range of 0 to 20 L (liter), preferably 0.01 L to 10 L, more preferably 0.05 L to 5 L, even more preferably 0.1 L to 3 L, and particularly preferably 0.2 L to 2 L per 1 mol of the raw material compound represented by the general formula (1), but it is not limited to these.

(Reaction Temperature)

Next, the reaction temperature in the method of the present invention will be described.

The reaction temperature in the method of the present invention is, for example, in a range of −10° C. (minus 10° C.) to 80° C., preferably 0° C. to 40° C., more preferably 5° C. to 35° C., even more preferably 5° C. to 25° C., particularly preferably 10° C. to 25° C. from the standpoint of suppression of by-product, safety, or the like.

The reaction pressure in the method of the present invention may be any of reduced pressure, increased pressure, or normal pressure, but it is preferable to implement the method at normal pressure.

(Reaction Time)

Next, the reaction time in the method of the present invention will be described.

The reaction time in the method of the present invention may be, for example, in a range of usually from 0.5 hours to 100 hours, preferably from 1 hour to 48 hours, more preferably from 2 hours to 48 hours, even more preferably from 3 hours to 48 hours, even more preferably from 4 hours to 48 hours, and particularly preferably from 4 hours to 12 hours from the standpoint of suppression of by-product, safety, or the like.

EXAMPLES

Next, the present invention will be specifically described with reference to Examples, but the present invention is not intended to be limited to these Examples in any way.

Example 1

Production of Diethyl Ketomalonate (Reaction at pH 5 to 8)

(1) In 100 g of water, 30 g (0.187 mol) of diethyl malonate was suspended, the pH was adjusted to 10 with a few drops of a 5% aqueous solution of sodium hydroxide and the liquid temperature was set to 10° C.

(2) In another reactor, 45% aqueous solution of sodium chlorate (402 g), 35% hydrochloric acid (100 mL), and 35% hydrogen peroxide (84 mL) were added while keeping at 35° C., and bubbling was performed by introducing air into the reactor so as to generate chlorine dioxide gas having a concentration of 8 vol % and a purity of 99%.

(3) The introduction of chlorine dioxide gas generated in (2) above into the reactor of (1) above containing suspended diethyl malonate was started via an inlet tube, and the chlorine dioxide gas was blown into the reactor over 5 hours at from 13° C. to 18° C. while maintaining the pH at from 5 to 8 by the appropriate dropwise addition of the 5% aqueous solution of sodium hydroxide. The amount of the 5% aqueous solution of sodium hydroxide used was 180 g.

(4) An aqueous solution of sodium thiosulfate was added to the homogeneous solution after the completion of the reaction to reduce residual chlorine dioxide, and the extraction was performed with ethyl acetate. Ethyl acetate was distilled off from the extract by means of a rotary evaporator, and toluene was added to the residual oil obtained and dehydration was performed under reflux. Toluene was distilled off so as to obtain 28.9 g of diethyl ketomalonate (diethyl mesoxalate) as the desired product. The purity determined by gas chromatography was 99.7% and the yield was 89%.

Diethyl ketomalonate (diethyl mesoxalate);

$^1$H NMR (300 MHz, CDCl$_3$) δ ppm: 4.39 (q, J=6.0 Hz, 2H), 1.36 (t, J=6.0 Hz, 3H).

$^{13}$C NMR (300 MHz, CDCl$_3$) δ ppm: 178.2, 160.2, 63.5, 13.9.

GC-MS (EI) m/z: 174 [M]$^+$.

Example 2

Production of Diethyl Ketomalonate (Reaction at pH Around 10)

In 100 g of water, 30 g (0.187 mol) of diethyl malonate was suspended, the pH was adjusted to 10 with a few drops of a 5% aqueous solution of sodium hydroxide and the liquid temperature was set to 10° C. Thereafter, blowing in 8 vol % chlorine dioxide gas was started in the same manner as in Example 1, and the chlorine dioxide gas was blown into the reactor over 5 hours at from 13° C. to 18° C. while maintaining the pH at around 10 by the appropriate dropwise addition of the 5% aqueous solution of sodium hydroxide. The amount of the 5% aqueous solution of sodium hydroxide used was 180 g.

After the reaction was completed, the reaction mixture was treated in the same manner as in Example 1 so as to obtain 28.1 g of diethyl ketomalonate (diethyl mesoxalate) as the desired product. The purity determined by gas chromatography was 88.1% and the yield was 76%. Diethyl 2,2-dichloromalonate was contained as a major impurity. It is possible to identify diethyl 2,2-dichloromalonate by a method known to those skilled in the art since it is a known compound.

Diethyl ketomalonate (diethyl mesoxalate);

$^1$H NMR (300 MHz, CDCl$_3$) δ ppm: 4.39 (q, J=6.0 Hz, 2H), 1.36 (t, J=6.0 Hz, 3H).

$^{13}$C NMR (300 MHz, CDCl$_3$) δ ppm: 178.2, 160.2, 63.5, 13.9.

Diethyl 2,2-dichloromalonate;

$^1$H NMR (300 MHz, CDCl$_3$) δ ppm: 4.36 (q, J=6.0 Hz, 2H), 1.33 (t, J=6.0 Hz, 3H).

$^{13}$C NMR (300 MHz, CDCl$_3$) δ ppm: 163.0, 100.5, 64.5, 13.6.

Comparative Example 1

Investigation on Production of Diethyl Ketomalonate
(Method without pH Control)

In 100 g of water, 30 g (0.187 mol) of diethyl malonate was suspended, and the liquid temperature was set to 10° C. Thereafter, blowing in 8 vol % chlorine dioxide gas was started in the same manner as in Example 1, and the chlorine dioxide gas was blown into the reactor over 5 hours at from 13° C. to 18° C.

The reaction mixture after the completion of blowing in was separated into two layers of an oil layer and an aqueous layer, and the pH of the aqueous layer was 2. The result of the analysis by gas chromatography indicated that the content of diethyl ketomalonate (diethyl mesoxalate) as the desired product was 1.8% and that of diethyl malonate of the remained raw material was 96.0%.

($^1$H Nuclear Magnetic Resonance Spectrum ($^1$H-NMR))

$^1$H nuclear magnetic resonance spectroscopy ($^1$H-NMR) was performed using a model: JNM-LA300 FT NMR SYSTEM (manufactured by JEOL Ltd.) and an internal standard substance: tetramethylsilane or chloroform.

(Analytical Method by Gas Chromatography (GC))

GC analysis was performed using a model: 6890N Network GC System (manufactured by Agilent Technologies, Inc.). With regard to the analytical method by GC, the following documents can be referred, as desired.

(a): "Shin Jikken Kagaku Koza 9, Bunseki kagaku II (A New Course in Experimental Chemistry 9, Analytical Chemistry II)", edited by The Chemical Society of Japan, pp. 60 to 86 (1977), published by IIZUMI Shingo, Maruzen Co., Ltd. (for example, it is possible to refer to pp. 66 with respect to liquids for a stationary phase to be usable for a column.)

(b): "Jikken Kagaku Koza 20-1, Bunseki kagaku (A Course in Experimental Chemistry 20-1, Analytical Chemistry)", edited by The Chemical Society of Japan, 5th edition, pp. 121 to 129 (2007), published by MURATA Seishiro, Maruzen Co., Ltd. (for example, it is possible to refer to pp. 124 to 125 with respect to the specific usage of hollow capillary separation columns.)

(Gas Chromatography-Mass Spectrometry (GC-MS))

GC-MS analysis was performed using a model: 6890N Network GC System (manufactured by Agilent Technologies, Inc.) as the GC analyzer and a model: 5973N MSD (manufactured by Agilent Technologies) as the mass detector.

(Method of Measuring pH)

The pH was measured by a glass electrode type hydrogen ion concentration indicator. As the glass electrode type hydrogen ion concentration indicator, specifically, for example, a type: Personal pH/ORP meter PH72 (manufactured by Yokogawa Electric Corporation), a type: HM-20P (manufactured by DKK-TOA CORPORATION), or the like can be used.

(Analytical Method of Chlorine Dioxide Gas)

With regard to the gas concentration and gas purity of chlorine dioxide gas, the quantitative analysis of chlorine dioxide gas was performed by the iodometric titration known to those skilled in the art. For example, the iodometric titration of chlorine dioxide gas can be performed by the following procedure; chlorine dioxide gas is absorbed to a 5 to 10% aqueous solution of potassium iodide having a pH of 7 or 8 adjusted with phosphate buffer. The titration of free iodine is performed with a 10 N aqueous solution of sodium thiosulfate using starch as an indicator. Thereafter, the solution after titration is adjusted to be acidic with 2 N sulfuric acid or the like. The titration of free iodine is performed in the same manner.

INDUSTRIAL APPLICABILITY

The method of the present invention provides a novel industrial process for production of ketomalonic acid compound or a hydrate thereof such as a ketomalonic acid diester which is used in the production of pharmaceuticals and agricultural chemicals as a raw material when producing a pyrazine-2-one-3-carboxylic acid ester derivative by reacting with a diamine and also as a raw material compound when producing a quinoxalinone derivative from an aromatic diamine. The method of the present invention is suitable for the safe and efficient production of a ketomalonic acid compound represented by the general formula (2) or a hydrate thereof by an industrial process and is useful in the organic chemical industry including pharmaceuticals, agricultural chemicals and the like.

The invention claimed is:

1. A method of producing a ketomalonic acid compound represented by the general formula (2)

[Chemical Formula 2]

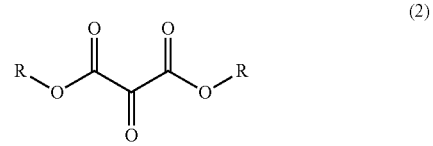

(2)

(wherein Rs may be the same or different from each other, and each represents a hydrogen atom, an alkyl group which optionally has substituent(s), a cycloalkyl group which optionally has substituent(s), an aromatic hydrocarbon group which optionally has substituent(s), or an aromatic heterocyclic group which optionally has substituent(s), and the two Rs may bind to each other to form a ring) or a hydrate thereof by reacting a malonic acid compound represented by the general formula (1)

[Chemical Formula 1]

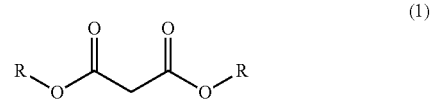

(1)

(wherein R is the same as described above) with chlorine dioxide.

2. The method of producing a ketomalonic acid compound or a hydrate thereof according to claim 1, wherein the reaction of the malonic acid compound with chlorine dioxide is conducted at pH in the range of 5 to 10.

3. The method of producing a ketomalonic acid compound or a hydrate thereof according to claim 1, wherein the reaction of the malonic acid compound with chlorine dioxide is conducted at pH in the range of 5 to 8.

4. The method of producing a ketomalonic acid compound or a hydrate thereof according to claim 1, wherein the reaction of the malonic acid compound with chlorine dioxide is conducted at pH in the range of 6 to 8.

5. The method of producing a ketomalonic acid compound or a hydrate thereof according to claim 1, wherein the pH is controlled using a pH adjusting agent.

6. The method of producing a ketomalonic acid compound or a hydrate thereof according to claim 5, wherein an inorganic base is used as the pH adjusting agent.

7. The method of producing a ketomalonic acid compound or a hydrate thereof according to claim 5, wherein an alkali metal hydroxide is used as the pH adjusting agent.

8. The method of producing a ketomalonic acid compound or a hydrate thereof according to claim 5, wherein sodium hydroxide is used as the pH adjusting agent.

9. The method of producing a ketomalonic acid compound or a hydrate thereof according to claim 1, wherein the reaction of the malonic acid compound with chlorine dioxide is conducted at pH in the range of 5 to 10, wherein the pH is controlled using sodium hydroxide as a pH adjusting agent.

10. The method of producing a ketomalonic acid compound or a hydrate thereof according to claim 1, wherein the reaction of the malonic acid compound with chlorine dioxide is conducted at pH in the range of 5 to 8, wherein the pH is controlled using sodium hydroxide as a pH adjusting agent.

11. The method of producing a ketomalonic acid compound or a hydrate thereof according to claim 1, wherein the reaction of the malonic acid compound with chlorine dioxide is conducted at pH in the range of 6 to 8, wherein the pH is controlled using sodium hydroxide as a pH adjusting agent.

12. The method of producing a ketomalonic acid compound or a hydrate thereof according to claim 1, wherein R in the general formula (1) is a $C_1$ to $C_4$ alkyl group.

13. The method of producing a ketomalonic acid compound or a hydrate thereof according to claim 1, wherein R in the general formula (1) is a methyl or an ethyl.

\* \* \* \* \*